（12） United States Patent
Zhang et al.

(10) Patent No.: US 7,892,478 B2
(45) Date of Patent: Feb. 22, 2011

(54) CATHETER BALLOON MOLD FORM AND MOLDING PROCESS

(75) Inventors: Ken Xiao Kang Zhang, Maple Grove, MN (US); Jeffrey S. Lindquist, Maple Grove, MN (US); Victor L. Schoenle, Greenfield, MN (US); Scott Schewe, Eden Prairie, MN (US); David Parsons, Princeton, MN (US); Nao Lee, Brooklyn Park, MN (US); Ying Xiong, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2009 days.

(21) Appl. No.: 10/827,494

(22) Filed: Apr. 19, 2004

(65) Prior Publication Data

US 2005/0233025 A1 Oct. 20, 2005

(51) Int. Cl.
  *B29C 49/00* (2006.01)
(52) U.S. Cl. ........................................ 264/535; 264/523
(58) Field of Classification Search ........................ None
  See application file for complete search history.

(56) References Cited

U.S. PATENT DOCUMENTS

| 641,494 | A |   | 7/1902  | Wilkins et al. ........... 604/46.01 |
| 3,766,358 | A | * | 10/1973 | Gass-Erb ..................... 392/498 |
| 4,340,344 | A |   | 7/1982  | Aston et al. .................. 425/149 |
| 4,490,421 | A |   | 12/1984 | Levy .......................... 428/36.9 |
| 4,906,244 | A |   | 3/1990  | Pinchuk et al. ............. 606/194 |
| 4,950,239 | A |   | 8/1990  | Gahara et al. .............. 604/96.01 |
| 5,223,205 | A |   | 6/1993  | Jackowski et al. .......... 264/521 |
| 5,236,659 | A |   | 8/1993  | Pinchuk et al. ............. 264/573 |
| 5,264,260 | A |   | 11/1993 | Saab .......................... 428/35.5 |
| 5,328,468 | A |   | 7/1994  | Kaneko et al. ......... 604/103.13 |
| 5,344,400 | A |   | 9/1994  | Kaneko et al. ......... 604/103.06 |
| 5,370,618 | A |   | 12/1994 | Leonhardt |
| 5,500,180 | A |   | 3/1996  | Anderson et al. ........... 264/532 |
| 5,522,961 | A | * | 6/1996  | Leonhardt .................... 156/252 |
| 5,556,383 | A |   | 9/1996  | Wang et al. ............. 604/103.11 |
| 5,792,415 | A |   | 8/1998  | Hijlkema .................... 264/530 |
| 5,833,657 | A |   | 11/1998 | Reinhardt et al. ...... 604/101.02 |
| 5,853,389 | A |   | 12/1998 | Hijlkema ............... 604/103.07 |
| 5,948,345 | A |   | 9/1999  | Patel et al. .................. 264/529 |
| 5,951,941 | A |   | 9/1999  | Wang et al. ................. 264/523 |

(Continued)

FOREIGN PATENT DOCUMENTS

WO 96/12516 5/1996

(Continued)

OTHER PUBLICATIONS

Communication relating to the results of the Partial International Search, PCT /US05/05475 (2 pgs).

*Primary Examiner*—Monica A Huson
(74) *Attorney, Agent, or Firm*—Vidas, Arrett & Steinkraus

(57) ABSTRACT

An immersion mold for a medical device balloon. The mold has a cavity adapted to receive a hollow parison expandable therein to form the balloon. The cavity has a length, a first end, a second end, and a cavity wall with inner and outer surfaces. The mold form cavity wall is provided with one or a plurality of through-holes along the length thereof to facilitate entrance and egress of a heated fluid.

18 Claims, 4 Drawing Sheets

U.S. PATENT DOCUMENTS

| | | | |
|---|---|---|---|
| 6,073,540 A * | 6/2000 | Garrett | 99/330 |
| 6,146,356 A | 11/2000 | Wang et al. | 604/96.01 |
| 6,168,748 B1 | 1/2001 | Wang et al. | 264/523 |
| 6,242,063 B1 | 6/2001 | Ferrera et al. | 428/35.2 |
| 6,270,522 B1 | 8/2001 | Simhambhatla et al. | 623/1.11 |
| 6,284,333 B1 | 9/2001 | Wang et al. | 428/35.5 |
| 6,290,485 B1 | 9/2001 | Wang | 425/470 |
| 6,328,710 B1 | 12/2001 | Wang et al. | 604/96.01 |
| 6,514,450 B1 | 2/2003 | Wang et al. | 264/513 |
| 6,561,788 B1 | 5/2003 | Gaudoin | 425/522 |
| 6,572,813 B1 | 6/2003 | Zhang et al. | 264/519 |
| 6,596,219 B2 | 7/2003 | Dutta et al. | 264/515 |
| 6,620,128 B1 | 9/2003 | Simhambhatla | 604/97.01 |
| 6,641,694 B1 | 11/2003 | Lee | 156/244.14 |
| 6,645,422 B2 | 11/2003 | Jung, Jr. et al. | 264/530 |
| 6,696,121 B2 | 2/2004 | Jung, Jr. et al. | 428/35.7 |
| 6,863,856 B1 | 3/2005 | Mahoney et al. | 264/231 |
| 2005/0127561 A1 | 6/2005 | Eberl et al. | 264/212 |

FOREIGN PATENT DOCUMENTS

WO  98/03218  1/1998

* cited by examiner

CATHETER BALLOON MOLD FORM AND MOLDING PROCESS

FIELD OF THE INVENTION

This invention pertains to a mold apparatus for forming medical device parts such as balloons employed on catheters, endoscopes and the like.

BACKGROUND OF THE INVENTION

U.S. Pat. No. 4,490,421 Levy, and U.S. Pat. No. 5,264,260, Saab, describe PET balloons. U.S. Pat. No. 4,906,244, Pinchuk et al, and U.S. Pat. No. 5,328,468, Kaneko, describe polyamide balloons. U.S. Pat. No. 4,950,239, Gahara, and U.S. Pat. No. 5,500,180, Anderson et al describe balloons made from polyurethane block copolymers. U.S. Pat. No. 5,556,383, Wang et al, and U.S. Pat. No. 6,146,356, Wang et al, describe balloons made from polyether-block-amide copolymers and polyester-block-ether copolymers. U.S. Pat. No. 6,270,522, Simhambhatla, et al, describes balloons made from polyester-block-ether copolymers of high flexural modulus. U.S. Pat. No. 5,344,400, Kaneko, describes balloons made from polyarylene sulfide. U.S. Pat. No. 5,833,657, Reinhart et al, describes balloons having a layer of polyetheretherketone. All of these balloons are produced from extruded tubing of the polymeric material by a blow-forming radial expansion process.

A typical method for forming medical device balloons includes molding the balloon from a hollow parison, for instance an extruded tubular parison. The mold form for such processes is adapted to receive the parison of thermoplastic material and has a cavity into or through which the parison extends. Heat is applied to the mold, for instance by immersion in a heated fluid, to soften the thermoplastic material. Concurrently, or in some sequence of heating and pressurization, the parison is pressurized to radially expand the softened thermoplastic material until it contacts and conforms to the shape of the cavity. This typical method may be practiced in a variety of known ways, for instance with or without an axial stretch step, which may be performed concurrent with or prior to radial expansion and at temperature above or below a glass transition temperature. The parison may be expanded in several steps, each of which may be accompanied by a prior or concurrent axial stretching step. A heat setting step or an annealing step may be performed after the balloon has been molded.

Mold forms for medical device balloons are typically provided with a highly polished or glassy cavity surface which is unbroken, at least over the body surface. In some cases, however a simple heated tube of larger diameter than the parison is used, so that the balloon end cones are free-formed. In a further alternative a balloon may be free-blown in a heated media with cone end forms used to confine the balloon ends.

High strength medical device balloons formed in the manner used for such applications as angioplasty and stent placement in cardiovascular vessels are well known. Typically such balloons are designed to provide a nominal inflated diameter of 6 mm or less. Recently, applications for even larger balloons of similar high strength have been identified.

WO 98/03218 describes techniques for preparing large diameter balloons (5-30 mm dia.), using tubular parisons formed of certain block copolymer materials and incorporating an annealing technique to widen the range of diameters obtainable over the range of useful inflation pressures. The balloons of WO 98/03218 are useful in gastrointestinal surgical procedures.

As balloon size increases, the increasing distance between the walls of the mold and the parison within the mold can cause a higher variability in the balloons obtained, possibly due to increased variability in the location of initiation. The ability to control the initiation location is typically difficult and delicate, as control of initiation requires control of the temperature gradient location within the mold. Conventional fluid-heated immersion molding devices do not allow for repeatable, accurate control of molding initiation location. With larger diameter balloons, this lack of control can negatively affect properties and yields. Balloon properties which may be negatively affected include wall thickness uniformity, position of key transitions associated with cone wall mass removal, and ultimately balloon performance, ability to be delivered, and overall balloon consistency. Therefore a need remains for improvements in balloon blowing processes, particularly for large diameter balloons.

SUMMARY OF THE INVENTION

The present invention is directed to a novel mold design for preparing medical device balloons to a balloon blowing process, and to balloons prepared by the process.

In one aspect the invention is directed to an immersion mold for a medical device balloon, the mold having a cavity adapted to receive a hollow parison expandable therein to form the balloon, wherein the mold form cavity wall is provided with at least one through-hole along the length thereof to facilitate entrance and egress of a heated fluid.

In another aspect the invention is directed to a method of forming a medical device comprising the steps of placing a parison in a mold having a cavity with a wall form substantially conforming to the desired shape of said device, immersing the mold in a heated liquid fluid to heat the parison, and pressurizing the parison to radially expand the parison to contact the walls of the mold cavity, wherein:

the mold cavity wall contains at least one through-hole therein through which the heated liquid fluid enters the mold cavity to directly contact the parison when the mold is immersed in the heated fluid and through which heated liquid fluid that has entered the mold cavity is expelled therefrom when the parison is radially expanded.

In use, the heated fluid enters the mold cavity through the through-holes in the wall to directly contact the parison when the mold is immersed in the heated fluid. When the parison is radially expanded the heated fluid that has entered the mold cavity is expelled from the mold cavity via the same route.

Balloons formed using a mold form of the invention or according the process of the present invention constitute further aspects of the invention. Still further aspects of the invention are described or are readily apparent from the accompanying drawings, detailed description and claims.

DETAILED DESCRIPTION OF PREFERRED EMBODIMENTS

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

Figure 1:
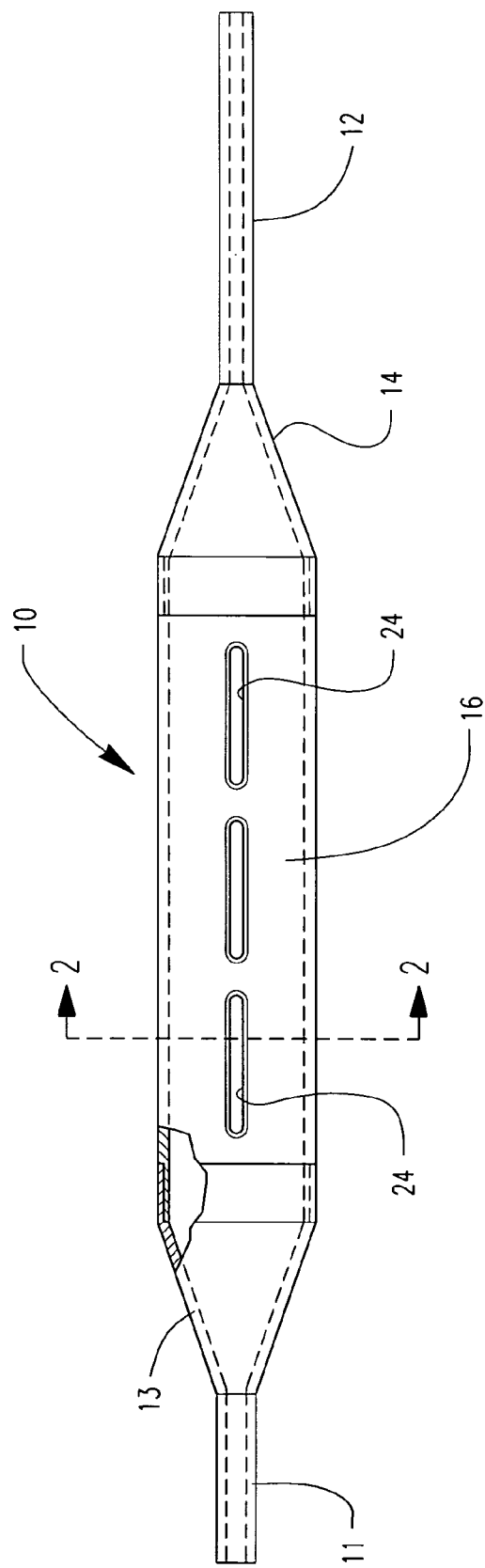
FIG. 1 is an exterior side view, with partial cutaway, of a mold form according to one embodiment of the invention.
Figure 2:
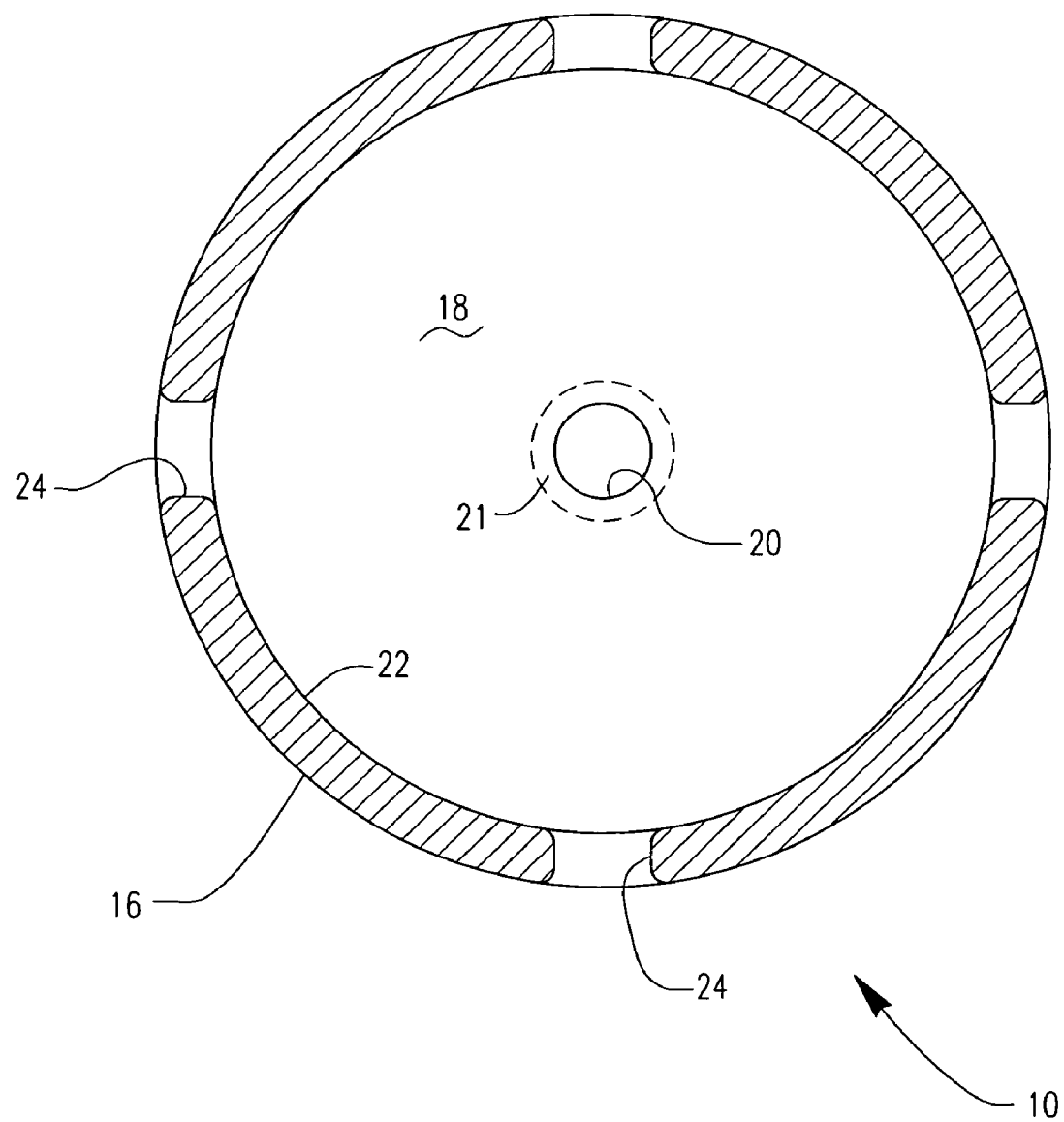
FIG. 2 is a sectional view taken along line 2-2 of FIG. 1.

Referring to FIGS. 1 and 2, there is shown an immersion mold form 10 according to one embodiment of the invention. Mold 10 has generally tubular end regions 11, 12, cone regions 13, 14 and a body region 16. At least one of the end regions 11, 12 is open to allow insertion of a parison. Typically the parison will be an extruded polymeric tube member which is designed to be extended through both end regions. The mold form 10 is adapted to be heated by immersion in a heated fluid media.

In accordance with the specific embodiment of the invention depicted in FIGS. 1-2, the interior cavity 18 of mold form 10 conforms generally to the exterior shape of the mold. Thus, the end region 12 has a corresponding interior surface 20, of substantially constant diameter; the cone region 14 has a corresponding inner surface 21 which slopes outwardly to a larger diameter at its junction with the cylindrical inner surface 22; and, inner surface 22, in turn, has the generally cylindrical shape of the exterior of the mold in the body region 16. It should be noted, however, that the balloon form is defined by the inner surfaces of the mold form cavity 18, not the exterior configuration. Consequently, it is not necessary that the outer surface correspond even in a general way to the shape of the inner surface. Moreover, more complex shapes especially in the body and/or cone regions may be employed. See for instance U.S. Pat. No. 6,290,485.

Figure 4:
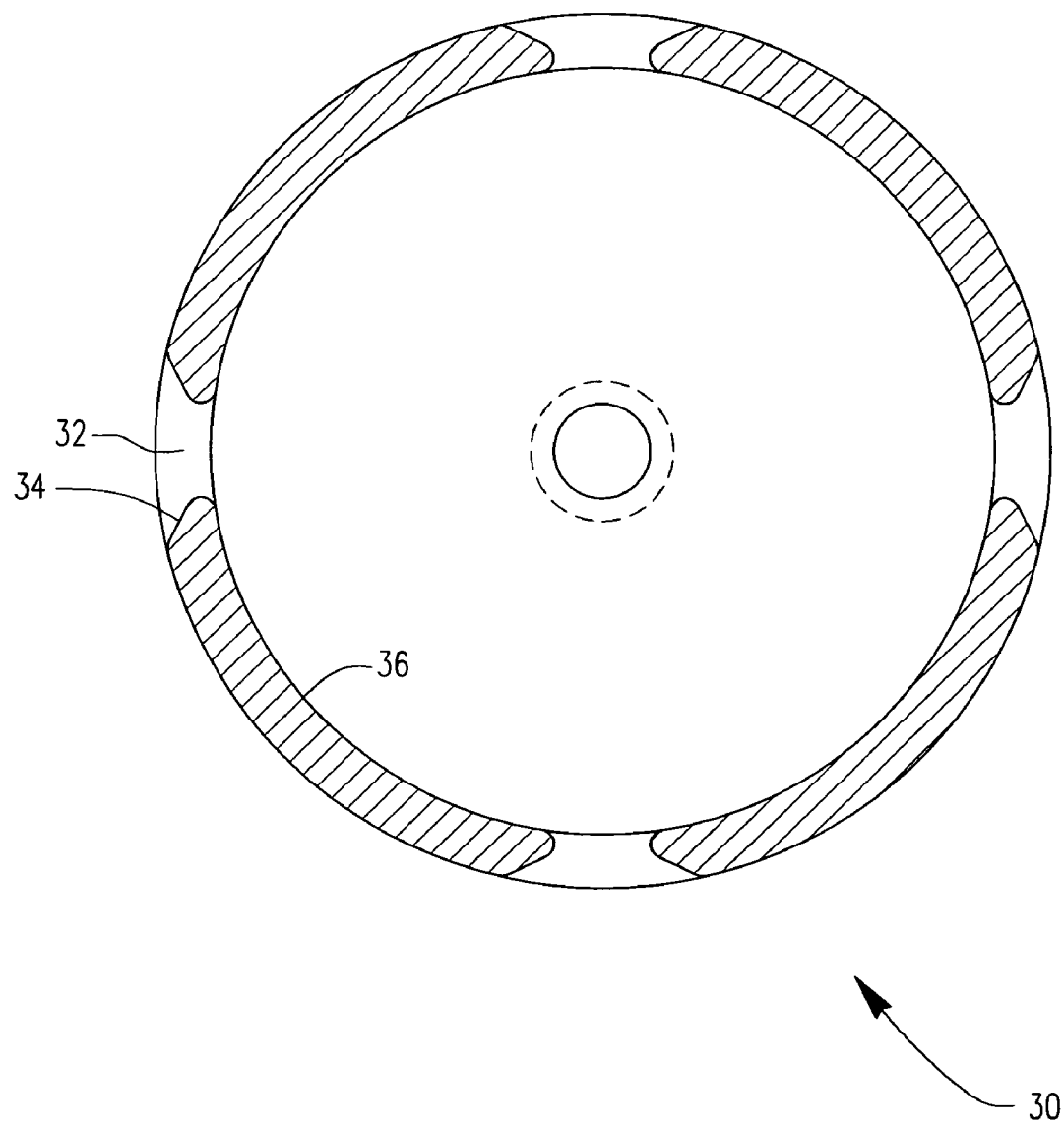
FIG. 4 is a sectional view taken along line 4-4 of FIG. 3.

The mold form may be configured to open or disassemble, to facilitate removal of the formed balloon. For a mold design as depicted in FIGS. 1-2 a segmented configuration, for instance as depicted in the cut-away portion of FIG. 1 or as depicted in FIG. 4 of U.S. Pat. No. 6,328,710, may be employed. Clam shell opening mechanisms, or other mold designs which mate two longitudinal sections, may also be employed in designing mold forms of the invention A characterizing feature of the inventive balloon molds is the presence of at least one, preferably more than one, through-hole that extends through the wall of the mold and opens into the inner cavity. In FIGS. 1 and 2 these through-holes are depicted at 24 and are disposed longitudinally relative to the central axis of the mold form, and spaced evenly around the circumference. Other patterns, however, are practical and can be readily implemented without departing from the invention. The location may be anywhere in the body, cone, and/or waist portions of the mold. The through-holes provide means for the heating media, typically heated water or oil, to enter the mold as the parison is dipped from one end down into a bath of the heating media. In this way heat is transferred much more directly to the parison.

The through-holes desirably will be of sufficiently large size that a reproducibly more rapid thermal transfer is obtained as fluid flows in and out of the mold. On the other hand the through-hole dimensions should ordinarily not be so large that the parison material substantially intrudes into the holes as it is brought into contact with the chamber walls. Intrusion of parison material into the through-holes can provide the molded balloon with creases or dimples, which may be undesirable in some balloons. In many cases, however, minor crease or dimple patterns which may be expected in balloons formed in the inventive mold forms are usually acceptable. For at least some types of balloons crease or dimple patterns may even be desirable, for instance, to facilitate refolding of the balloon after inflation or to provide mounting sites for blade assemblies of a cutting balloon. In general, for rectangles and other holes having major and minor dimensions, the minor dimension of the through-holes may be from about 0.1 mm to about 1.5 mm, for instance from about 0.2 to about 0.5 mm and the major dimension may be from about 0.2 mm to the full length or circumference of the mold form subject, the latter case of course being subject to the provision of a mechanism for holding and maintaining the mold in assembled form. Exemplary such major dimensions include for instance 0.5-10 cm. Suitable diameters for circular holes may be for instance from 0.1 mm to about 1.5 mm, for instance about 0.2 to about 0.7 mm.

The rapidity of the thermal transfer can be further facilitated by agitation of the fluid and/or molding apparatus vibration, for instance by ultrasonic vibration.

The location of the through-holes may be such that, for a given dipping process, the heated fluid has had an opportunity to enter the chamber and contact the parison to the depth of dipping by the time that initiation of blowing is desired. Also suitably, the through-holes may be spaced along the length of the mold so that heating media entering the mold is readily displaced out the same holes as the parison expands to fill the chamber. In the embodiments of the Figures, longitudinally oriented slots are provided with parallel sides and rounded ends. Alternative arrangements are feasible, including helical and circumferential orientations. The longitudinal positions of slot through-holes may be staggered around the circumference so that at every location along the length of the body portion of the mold form at least one opening exists somewhere on the circumference.

Preferably at least two openings exist along the body length to facilitate both entrance of the heated fluid into the mold cavity and egress therefrom. In some cases it may be feasible to expel the fluid though one or both ends of the mold cavity.

In one embodiment, a titanium mold form for a balloon having a body cavity of about 8 mm diameter and 4 cm body length, was provided with a series of 4 longitudinally extending slot columns spaced equally around the circumference (i.e. at 90° intervals as shown in FIG. 2). Adjacent columns of slots were staggered with the number of slots alternating between three and four slots/column, moving around the circumference of the mold. Each slot had a width of approximately 0.5 mm and a length of approximately 6 mm. The mold could be used to prepare balloons of acceptable strength for angioplasty, gastrointestinal and/or stent placement applications.

Although longitudinally oriented slot holes are shown in the Figures, it should be understood that the through-holes can take virtually any shape and need not be longitudinally oriented. The holes may be circular, rectangular, diamond, square oval, or any other shape feasible for manufacture. Helical through-hole orientation should also normally be acceptable. In some cases longitudinally spaced slot holes whose long dimension is oriented circumferentially, rather than longitudinally, may also be effective.

Figure 3:
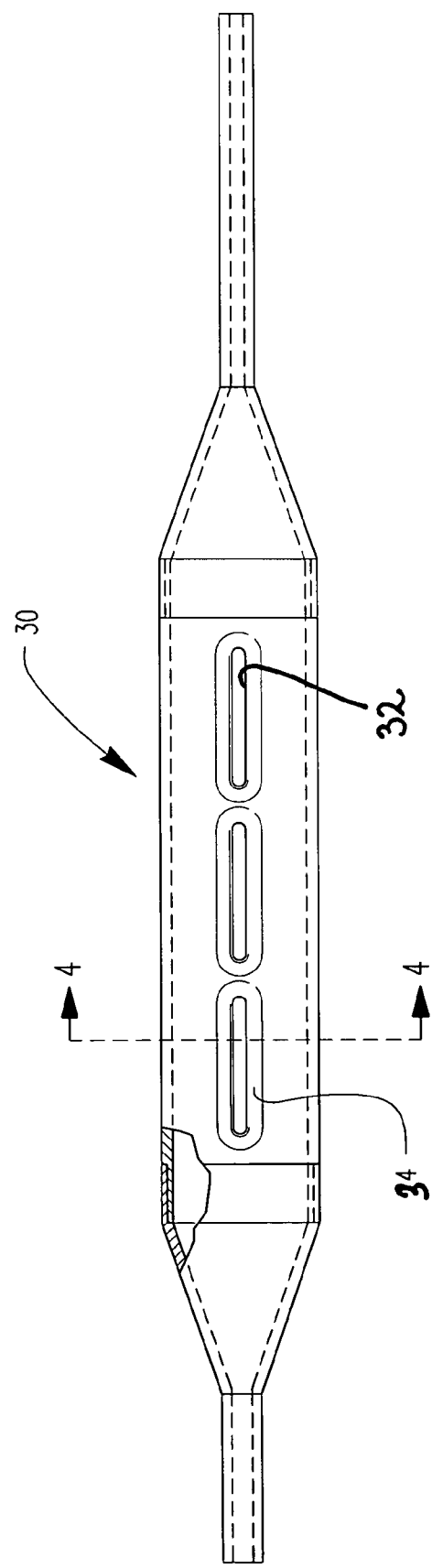
FIG. 3 is an exterior side view of a mold form according to a second embodiment of the invention.

FIGS. 3 and 4 depict another embodiment of the invention. Mold form 30 is substantially the same as mold form 10, except that the through-holes 32 have a chamfer 34 which flares outwardly from the opening at the surface of the inner cavity 36 to the outer surface of the mold. This design reduces the flow resistance of the heated media through the side holes to some extent, without enlargement of the through-hole profile at the mold cavity wall.

Mold forms of the invention may be made of any suitable material, preferably one which provides for a highly polished or glassy cavity surface. Metal, such as titanium or stainless steel, are exemplary materials. Glass and ceramic materials may also be employed. Composite and laminate materials are also suitable. Preferred are materials which have high heat conductivity, especially metals such as stainless steel, titanium, aluminum and the like.

The balloons are blown in the inventive molds using conventional procedures for immersion blow molding of catheter balloons. Such a process may include the steps of placing a parison in a mold having a cavity with a wall form substantially conforming to the desired shape of said device, immersing the mold in a heated fluid to heat the parison, and pressurizing the parison to radially expand the parison to contact the walls of the mold cavity. The heated fluid enters the mold cavity to directly contact the parison when the mold is immersed in the heated fluid. As the parison softens and is pressurized it expands, expelling the heated fluid that has entered the mold cavity therefrom and conforming itself to the mold cavity shape.

The heated fluid may be any fluid suited to the temperature of molding and the materials of the mold form and the parison. Water at a temperature of about 90° C. to about 99° C. is exemplary. Other fluids such as glycerol, mineral oil or silicone oil at the same or higher temperature are also known and can be employed in the invention. Between the various known fluids, those with relatively lower viscosities are preferred.

Any balloon material suited to molding may be employed in the inventive method. Balloon materials which may be advantageously employed in the invention are well known. Any material which can be molded from a parison may be feasibly employed in the invention. Such materials include polyesters such as PET, PEN and PBT, polyurethane block copolymers such as ISOPLAST 301, PELLETHANE 2363-75D, and other materials described in U.S. Pat. Nos. 4,950,239 or 5,500,180; polyamide block copolymers such as PEBAX 6333, PEBAX 7033 and PEBAX 7233, and other materials described in U.S. Pat. No. 5,556,383; polyamides such as nylon 12, nylon 11, nylon 10, and other materials described in U.S. Pat. No. 4,906,244; polymer blend materials such as single or multiphase blends of liquid crystal polymers in another polymer, such as described in U.S. Pat. 6,242,063, U.S. Pat. No. 6,284,333 or U.S. Pat. No. 6,596,219; and polyester elastomer balloons such as ARNITEL EM 740, HYTREL 8238, and other materials described in U.S. Pat. Nos. 5,556,383 or 6,270,522.

Direct transfer of heat from the heated fluid to the parison is thought to be more efficient than indirect transfer through the space between the mold cavity and the parison. Therefore the inventive mold forms are believed to facilitate a more consistent initiation point for blowing the balloons. As a result, more consistent and higher performance balloon components can be obtained in markedly improved yields. Without being bound thereto, it is believed that the invention obtains these benefits by improving thermal transfer of the hot fluid heat source to the interior of a large mold cavity. This improved thermal transfer is obtained by hot fluid delivery through the small channel orifices (through-holes) in the mold cavity. The direct contact of hot fluid with the parison is seen to provide a much more efficient transfer of thermal energy to the parison, thereby producing the reduced variability in balloon properties. This benefit becomes increasingly noticeable as balloon mold diameters increase above 5 mm, for instance with mold diameters about 6 mm to about 50 mm, especially those with diameters of about 8 mm or above.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to." Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. A method of forming a medical device comprising the steps of placing a parison in a mold having a cavity with a wall form substantially conforming to the desired shape of said device,
    immersing the mold in a heated liquid fluid to heat the parison, and
    pressurizing the parison to radially expand the parison to contact the walls of the mold cavity,
    wherein the mold cavity wall contains at least one through-hole therein through which the heated liquid fluid enters the mold cavity to directly contact the parison when the mold is immersed in the heated fluid and through which heated liquid fluid that has entered the mold cavity is expelled therefrom when the parison is radially expanded, the at least one through-hole havin a first dimension of at least about 0.1 mm and a second dimension of at least about 0.2 mm.

2. The method of claim 1 wherein the through-hole is formed as a slot.

3. The method of claim 1 wherein the through-holes are formed as longitudinally oriented slots.

4. The method of claim 3 wherein the slots are arranged in a plurality of circumferentially spaced columns.

5. The method of claim 4 wherein the slots of circumferentially alternating columns of slots are staggered longitudinally.

6. The method of claim 4 wherein the mold cavity wall has at least three of said circumferentially spaced columns of slots.

7. The method of claim 6 wherein the mold cavity wall has four of said circumferentially spaced columns of slots.

8. The method of claim 1 wherein the at least one through-hole has a dimension at the mold cavity wall inner surface which does not allow substantial penetration of the parison material therethrough when heated to the temperature of the heated fluid and pressurized at a pressure sufficient to expand the parison to contact the mold cavity wall.

9. The method of claim 1 wherein the at least one through-hole has a an oval, diamond or rectangular shape at the cavity wall inner surface.

10. The method of claim 1 wherein the mold cavity wall has a plurality of said through-holes arranged according to a pattern which extends circumferentially around the cavity wall.

11. The method of claim 1 wherein the mold cavity wall has a plurality of said through-holes arranged according to a pattern which extends helically around the cavity wall.

12. The method of claim 1 wherein the cavity has a portion having a diameter of at least 5 mm.

13. The method of claim 12 wherein said diameter is from about 8 mm to about 50 mm.

14. A method as in claim 1, further comprising agitating the heated fluid while the mold is immersed therein.

15. A method as in claim 1 further comprising vibrating the molding apparatus while the mold is immersed in the heated fluid.

16. A method as in claim 1 wherein the mold cavity wall contains a plurality of said through-holes therein.

17. The method of claim 1 wherein the heated liquid fluid is water, glycerol or an oil.

18. A method of forming a medical device comprising the steps of placing a parison in a mold having a cavity with a wall form substantially conforming to the desired shape of said device, immersing the mold in a heated liquid fluid to heat the parison, and pressurizing the parison to radially expand the parison to contact the walls of the mold cavity, wherein the mold cavity wall contains at least one through-hole therein through which the heated liquid fluid enters the mold cavity to directly contact the parison when the mold is immersed in the heated fluid and through which heated liquid fluid that has entered the mold cavity is expelled therefrom when the parison is radially expanded, the at least one through-hole being substantially circular and having a diameter of at least about 0.1 mm.

* * * * *